(12) United States Patent
Du et al.

(10) Patent No.: US 11,213,251 B2
(45) Date of Patent: Jan. 4, 2022

(54) DETECTION DEVICE

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Yufeng Du, Beijing (CN); Jiaxing Chen, Beijing (CN); Tong Li, Beijing (CN); Yufei Liu, Beijing (CN); Litao Fan, Beijing (CN); Hongyang Yu, Beijing (CN); Guangzhao Yang, Beijing (CN); Shuang Shi, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

(*) Notice: Subject to any disclaimer, the term of this patent is extended or adjusted under 35 U.S.C. 154(b) by 223 days.

(21) Appl. No.: 16/566,328

(22) Filed: Sep. 10, 2019

(65) Prior Publication Data
US 2020/0297278 A1      Sep. 24, 2020

(30) Foreign Application Priority Data

Mar. 22, 2019   (CN) .................. 201920379675.X

(51) Int. Cl.
*A61B 5/00*      (2006.01)
*A61B 5/145*    (2006.01)
(Continued)

(52) U.S. Cl.
CPC .......... *A61B 5/681* (2013.01); *A61B 5/14532* (2013.01); *A61B 5/15* (2013.01);
(Continued)

(58) Field of Classification Search
CPC . A61B 5/14532; A61B 5/150206; A61B 5/15; A61B 5/150305; A61B 5/150358;
(Continued)

(56) References Cited

U.S. PATENT DOCUMENTS

| | | | |
|---|---|---|---|
| 7,670,300 B2 * | 3/2010 | Vreeke | A61B 5/150213 600/583 |
| 8,333,715 B1 * | 12/2012 | Alferness | A61B 5/150519 600/584 |
| 2017/0188912 A1 * | 7/2017 | Halac | A61B 5/14532 |

FOREIGN PATENT DOCUMENTS

| | | | | |
|---|---|---|---|---|
| DE | 10057832 C1 * | 2/2002 | ....... | A61B 5/150435 |
| DE | 19758804 B4 * | 10/2009 | ......... | A61B 5/14514 |

(Continued)

OTHER PUBLICATIONS

Wang, Gang; Poscente, Michael D.; Park, Simon S.; Andrews, Christopher N.; Yadid-Pecht, Orly; Mintchev, Martin P.; Wearable Microsystem for Minimally Invasive, Pseudo-Continuous Blood Glucose Monitoring: The e-Mosquito; IEEE Transactions on Biomedical Circuits and Systems; vol. 11, No. 5 (Year: 2017).*

(Continued)

*Primary Examiner* — Eric F Winakur
*Assistant Examiner* — Alice Ling Zou
(74) *Attorney, Agent, or Firm* — Collard & Roe, P.C.

(57) ABSTRACT

A detection device is provided and the detection device includes: a body, including a first groove and a first opening; the first opening is on a first surface of the body and in communication with the first groove; a collector, configured to be at least partially accommodated into the first groove in a rotatable manner and being capable of rotating to allow at least part of the collector to extend out of the first opening in a process of detection; a test paper supplier, disposed on the first surface and configured to provide a test paper on a side of the first opening away from the first groove in the (Continued)

process of detection so as to collect a detection sample; and a detector, disposed on the first surface and configured to detect the test paper that has collected the detection sample.

16 Claims, 4 Drawing Sheets

(51) Int. Cl.
  *A61B 5/157* (2006.01)
  *A61B 5/15* (2006.01)
  *G06F 1/16* (2006.01)
(52) U.S. Cl.
  CPC ............ *A61B 5/157* (2013.01); *A61B 5/6824* (2013.01); *A61B 5/742* (2013.01); *G06F 1/163* (2013.01); *G06F 1/1684* (2013.01)
(58) Field of Classification Search
  CPC .............. A61B 5/150748; A61B 5/157; A61B 5/14546; A61B 5/145; A61B 5/681; A61B 5/6824; A61B 5/6831; A61B 2560/0462; A61B 5/150022; A61B 5/150244; A61B 5/151; A61B 5/15107; A61B 5/15113; A61B 5/15115; A61B 5/15117; A61B 5/15128; A61B 5/15126; A61B 5/1513; A61B 5/150152–15016; A61B 5/150267; A61B 5/150534; A61B 5/150633; A61B 5/150664; A61B 5/150709–150725; A61B 5/150687; A61B 5/150671; A61B 5/150236–150244; A61B 5/1468–1473; A61B 5/1411; A61M 5/003; A61M 2005/2026; A61M 5/2033; A61M 5/20
  See application file for complete search history.

(56) References Cited

FOREIGN PATENT DOCUMENTS

| | | | | |
|---|---|---|---|---|
| GB | 2331936 A | * | 6/1999 | ......... A61B 5/15109 |
| JP | 2001281242 A | * | 10/2001 | |
| WO | WO-0191634 A2 | * | 12/2001 | ....... A61B 5/150801 |

OTHER PUBLICATIONS

Translation of Item N (Year: 2021).*

* cited by examiner

DETECTION DEVICE

CROSS-REFERENCE TO RELATED APPLICATION

The present application claims priority to Chinese Patent Application No. 201920379675.X, filed Mar. 22, 2019, the disclosure of which is incorporated herein by reference in its entirety as part of the application.

TECHNICAL FIELD

The embodiments of the present disclosure relate to a detection device.

BACKGROUND

Current medical technology is still unable to cure diabetes, and can only control the occurrence and development of diabetes and its complications by stabilizing the blood sugar level.

SUMMARY

At least one embodiment of the present disclosure provides a detection device, which includes:

a body, comprising a first groove and a first opening, wherein the first opening is on a first surface of the body and in communication with the first groove;

a collector, configured to be at least partially accommodated in the first groove in a rotatable manner and being capable of rotating to allow at least part of the collector to extend out of the first opening in a process of detection;

a test paper supplier, disposed on the first surface and configured to provide a test paper on a side of the first opening away from the first groove in the process of detection so as to collect a detection sample; and a detector, disposed on the first surface and configured to detect the test paper that has collected the detection sample.

In some embodiments, the collector further comprises a first rotating shaft, and the collector is pivotably connected with the body through the first rotating shaft.

In some embodiments, the collector comprises a collecting part and a button operably connected to the collecting part, the button is disposed on a side of the collector facing the first surface in a case where the collector is in an accommodated state, wherein in the accommodated state, the collector is accommodated in the first groove, and the button is exposed in a case where the collector is rotated to be in an operating state.

In some embodiments, the collector comprises a front portion, a central portion and a rear portion, in a case where the collector is in the accommodated state, the collecting part is assembled on the rear portion, and an end portion of the collecting part is accommodated in the front portion;

the rear portion comprises a mechanical spring mechanism which is configured to eject the collecting part towards the front portion under an actuation of the button; and the button is disposed on the central portion and operably connected with the mechanical spring mechanism.

In some embodiments, the rear portion comprises a recess structure.

In some embodiments, the mechanical spring mechanism comprises a spring, and a side of the spring away from the collecting part is connected to the rear portion; and the detection device further comprises a base, wherein the base comprises a mounting part configured to assemble the collecting part, and a side of the spring close to the collecting part is connected to a side of the base away from the mounting part.

In some embodiments, the rear portion comprises a partition plate which is spaced from an end of the rear portion away from the collecting part, so as to confine the spring between the partition plate and the base;

the mechanical spring mechanism further comprises a pull rod, wherein the pull rod extends through the spring and is connected to the base on a side close to the collecting part, and the pull rod movably extends through the partition plate.

In some embodiments, the spring comprises a first spring and a second spring connected with the first spring;

the partition plate comprises a first partition plate and a second partition plate;

the first partition plate is configured to confine the first spring between the base and the first partition plate;

the second partition plate is configured to separate the second spring from the end of the rear portion away from the collecting part;

the first spring is configured to be compressed in a case where the collecting part is assembled on the rear portion and be released under the actuation of the button to eject the collecting part; and the second spring is configured to movably extend through the first partition plate and configured to generate an elastic force in a case where the first spring is released to retract the collecting part.

In some embodiments, the button comprises a release end; and the base comprises a clamping part, wherein the clamping part is configured to clamp the release end of the button.

In some embodiments, the detection device further comprises a spring sheet which is between the button and the clamping part, wherein the release end of the button is configured to be slidable on the spring sheet and be clamped by the clamping part in a case where the release end of the button slides to a first positioning point, so that the spring is in a compressed state.

In some embodiments, the test paper supplier is configured to provide, in the process of detection, a test paper on the side of the first opening away from the first groove and at a position corresponding to the collecting part of the collector that is in the operating state.

In some embodiments, the test paper supplier comprises a test paper rotating shaft; and the test paper rotating shaft is configured to accommodate the test paper and allow the test paper to extend out of a tail end of the test paper rotating shaft, and the test paper rotating shaft is also configured to be rotatably connected to the body.

In some embodiments, the test paper rotating shaft is configured to: accommodate the test paper into the detector in a case where the test paper rotating shaft rotates to a first position; and provide the test paper on the side of the first opening away from the first groove and at the position corresponding to the collecting part of the collector that is in the operating state in a case where the test paper rotating shaft rotates to a second position.

In some embodiments, the test paper supplier further comprises a driver which is configured to be connected with the test paper rotating shaft to drive the test paper rotating shaft to rotate.

In some embodiments, the driver comprises a servo motor, wherein the servo motor comprises an output shaft which is connected with the test paper rotating shaft.

In some embodiments, the detector comprises a second opening which is configured to allow the test paper to extend into the detector in a case where the test paper rotating shaft rotates to the first position.

In some embodiments, the body further comprises an accommodating part which comprises at least one partition.

In some embodiments, the detection device further comprises a carrier, wherein the carrier is configured to carry the body.

In some embodiments, the carrier comprises a wristlet.

In some embodiments, the body further comprises a display which is on a side of the body away from the first surface and configured to display a detection result.

BRIEF DESCRIPTION OF THE DRAWINGS

In order to clearly illustrate the technical solutions of the embodiments of the present disclosure, the drawings of the embodiments will be briefly described in the following; it is obvious that the described drawings are only related to some embodiments of the present disclosure and thus are not limitative of the present disclosure.

DETAILED DESCRIPTION

Figure 1:
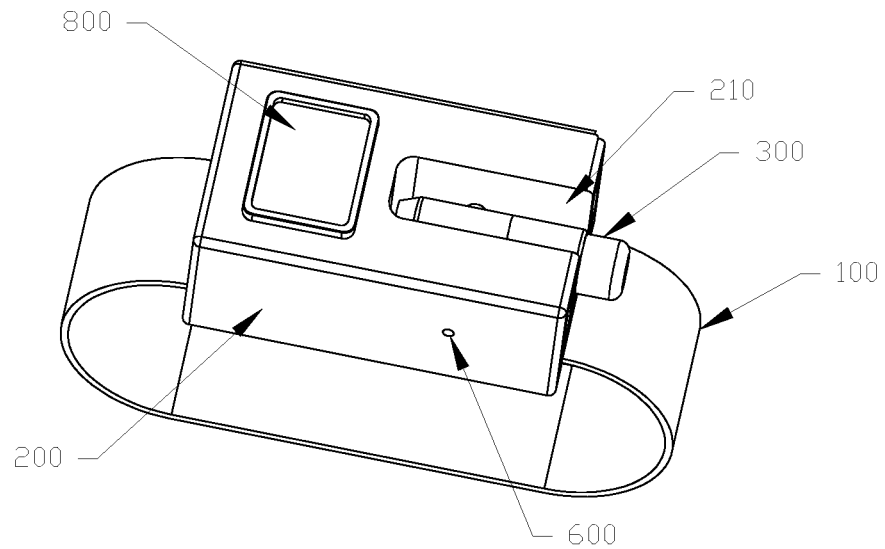
FIG. 1 is a schematic structural diagram illustrating the case where a blood collection pen of a blood sugar detection device provided by at least one embodiment of the present disclosure is in an accommodated state.

In order to make objects, technical details and advantages of the embodiments of the present disclosure apparent, the technical solutions of the embodiments will be described in a clearly and fully understandable way in connection with the drawings related to the embodiments of the present disclosure. Apparently, the described embodiments are just a part but not all of the embodiments of the present disclosure. Based on the described embodiments herein, those skilled in the art can obtain other embodiment(s), without any inventive work, which should be within the scope of the present disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for invention, are not intended to indicate any sequence, amount or importance, but distinguish various components. Also, the terms such as "a," "an," etc., are not intended to limit the amount, but indicate the existence of at least one. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

At present, patients can quickly self-test blood sugar by using capillary blood. Blood sugar self-test usually requires a blood sugar meter, a blood collection pen, a blood collection needle and a blood sugar test paper. The patient first needs to collect blood with the blood collection pen and the blood collection needle, and then drips the blood onto the test paper, and finally utilizes the blood sugar meter to obtain the blood sugar level. The blood sugar meter usually only has the blood sugar detecting function. The steps for performing the blood sugar test by using the blood sugar meter are complicated; the required parts are numerous; the use of the blood sugar meter is not convenient enough; and it is inconvenient to carry.

At least one embodiment of the present disclosure provides a detection device, which includes:

a body, including a first groove and a first opening, the first opening being disposed on a first surface of the body and in communication with the first groove;

a collector, configured to be at least partially accommodated in the first groove in a rotatable manner and being capable of rotating to allow at least part of the collector to extend out of the first opening in a process of detection;

a test paper supplier, disposed on the first surface and configured to provide a test paper on a side of the first opening away from the first groove in the process of detection to collect a detection sample; and a detector, disposed on the first surface and configured to detect the test paper that has collected the detection sample.

The detection device may be used for performing blood detection such as blood sugar measurement, blood fat detection and platelet detection, and may also be used for detecting other body fluids or tissues. No limitation will be given here in the embodiments of the present disclosure. Hereinafter, the detection device will be described by taking blood detection as an example.

Figure 2:
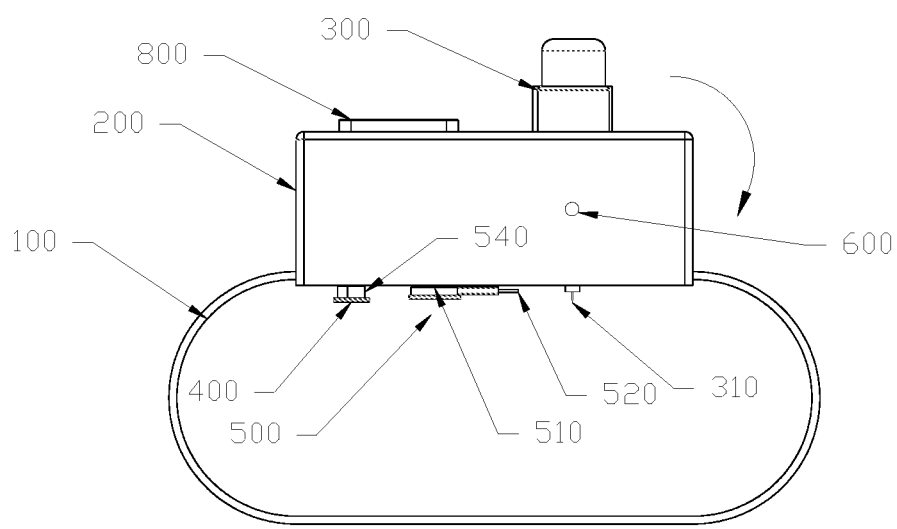
FIG. 2 is a schematic structural diagram illustrating the case where the blood collection pen of the blood sugar detection device provided by at least one embodiment of the present disclosure is in the operating state.
Figure 3:
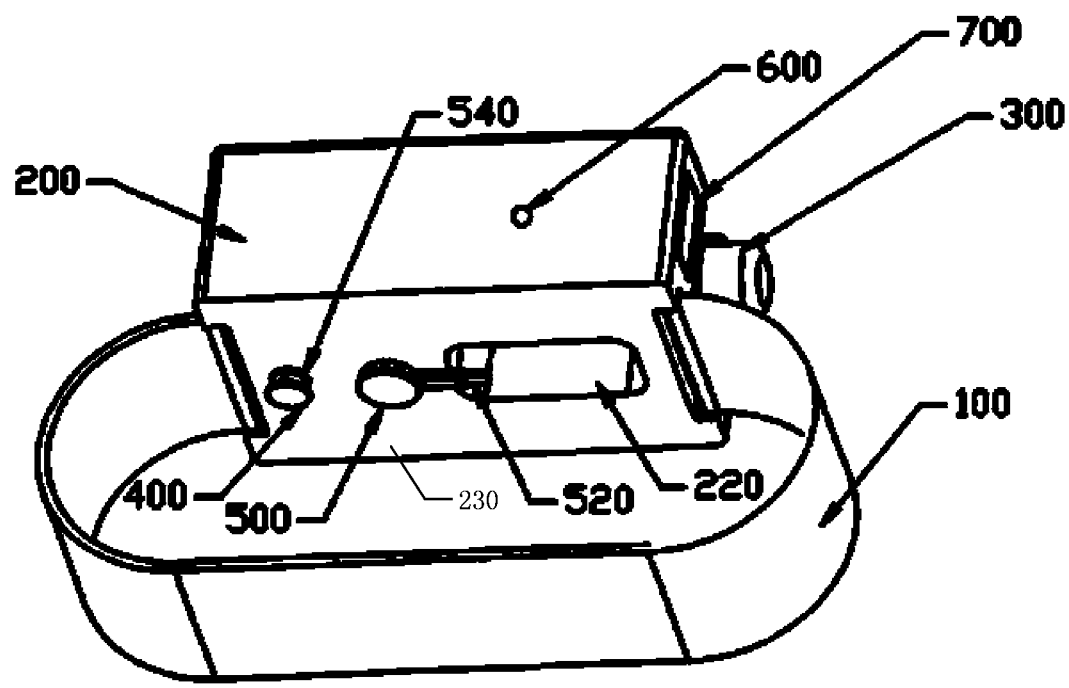
FIG. 3 is a schematic structural diagram of a side facing skin of the blood sugar detection device provided by at least one embodiment of the present disclosure.

FIG. 1 is a schematic structural diagram illustrating a case where a blood collection pen 300 of a blood sugar detection device provided by at least one embodiment of the present disclosure is in an accommodated state. FIG. 2 is a schematic structural diagram illustrating a case where the blood collection pen 300 of the blood sugar detection device provided by at least one embodiment of the present disclosure is in an operating state. FIG. 3 is a schematic structural diagram of a side facing skin of the blood sugar detection device provided by at least one embodiment of the present disclosure. As shown in FIGS. 1-3, at least one embodiment of the present disclosure provides a blood sugar detection device, which comprises: a carrier 100; a body 200, carried on the carrier 100 and provided with a first groove 210 and a first opening 220 which is disposed on a first surface 230 of the body 200 in communication with the first groove 210; a blood collection pen 300, at least partially accommodated into the first groove 210 in a rotatable manner, and a blood collection end of the blood collection pen 300 being capable of extending out of the first opening 220; a blood sugar detector 400, disposed on a side of the body 200 where the first opening 220 is located and configured to perform blood sugar detection on a test paper 520 that has collected blood; and a test paper supplier 500 disposed on the side of the body 200 where the first opening 220 is located and configured to provide the test paper 520 at the position below the first opening 220 during the blood sugar detection. The above-mentioned first surface 230 refers to a surface of the body 200 facing the skin to be pierced of the user in use. More specifically, when the user does not use the blood sugar detection device, the blood collection pen 300 may be accommodated into the first groove 210 by rotation, so as to reduce the volume of the blood sugar detection device, and then the blood sugar detection device is convenient to carry. When the user adopts the blood sugar detection device for blood sugar detection, by rotating the blood collection pen 300, a blood collection end of the blood collection pen 300 is extended out of the first opening 220 and pierces the skin; the test paper supplier 500 provides the test paper 520 below the first opening 220 (i.e., a side of the first opening 220 away from the first groove 210) to collect blood; the test paper 520 that has collected blood is placed on the blood sugar detector 400 to complete the blood sugar detection; and after the blood sugar detection is completed, the user rotates the blood collection pen 300 to be accommodated into the first groove 210. It should be understood that the blood collection pen 300 is only an example of the above-mentioned collector, and may also adopt other appropriate forms according to actual requirements, which is not limited in the embodiments of the present disclosure. In addition, blood is only an example of the above-mentioned detection sample. When the detection device is used for other detections, the detection sample may also be body fluids such as tissue fluids and saliva, or tissues such as cells and epidermis, and no limitation will be given here in the embodiments of the present disclosure. Similarly, the blood sugar detector 400 is also only an example of the above-mentioned detector, and no limitation will be given here in the embodiments of the present disclosure.

In the blood sugar detection device provided by at least one embodiment of the present disclosure, the blood collection pen 300, the blood sugar detector 400 and the test paper supplier 500 are integrated and may be accommodated onto the body 200 of the blood sugar detection device, so that the blood sugar detection device can be convenient to use and carry.

Figure 4:
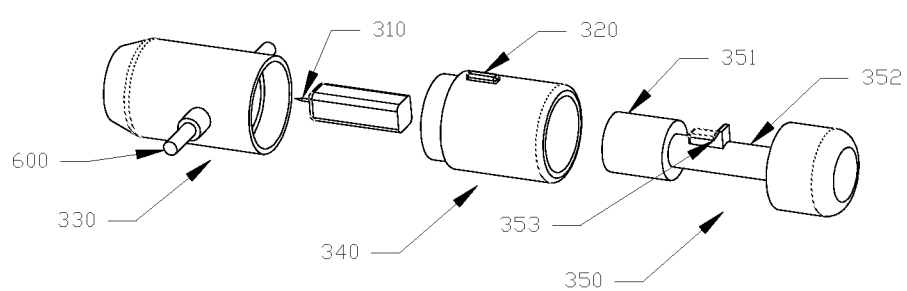
FIG. 4 is a schematic assembly diagram of the blood collection pen of the blood sugar detection device provided by at least one embodiment of the present disclosure.

In some embodiments, as shown in FIGS. 1 and 4, the blood collection pen 300 includes a first rotating shaft 600 and is pivotably connected with the body 200 through the first rotating shaft 600. More specifically, the first rotating shaft 600 is between side walls of the first groove 210, so that the blood collection pen 300 is capable of rotating around the first rotating shaft 600 to extend out of the first opening 220, and to rotate to a horizontal position relative to the body 200 and be accommodated into the first groove 210 after completing blood sugar detection, so as to reduce the volume of the blood sugar detection device and make the blood sugar detection device convenient to carry.

In some embodiments, the collector may include a collecting part and a button operably connected to the collecting part. As shown in FIG. 4, the blood collection pen 300 further includes a blood collection needle 310 for piercing the skin and a blood collection button 320 for controlling the ejection of the blood collection needle 310. The blood collection button 320 is disposed on a side of the blood collection pen 300 facing the human body (namely the side facing the first surface 230) in the case where the blood collection pen 300 is in the accommodated state of being accommodated into the first groove 210, so as to be not exposed and avoid the misoperation of the user. In the process of blood sugar detection, the blood collection pen 300 is rotated so that the blood collection end (for instance, the blood collection needle 310) of the blood collection pen 300 extends out of the first opening 220 below the first groove 210 (for instance, the blood collection pen 300 is in the operating state as shown in FIG. 2), so as to expose the blood collection button 320. In this case, the user pushes, rotates or presses the blood collection button 320, so that the blood collection needle 310 can be ejected to pierce the skin. It should be understood that the blood collection needle 310 is only an example of the collecting part, and the collecting part may also adopt other appropriate forms according to actual demands. In addition, the blood collection button 320 is also only an example of the button operably connected to the collecting part, and no limitation will be given here in the embodiments of the present disclosure.

It should be understood that in the case where the blood collection pen 300 is in the accommodated state, the blood collection pen 300 is accommodated into the first groove 210; and in the case where the blood collection pen 300 is in the operating state, the blood collection end (for example, the blood collection needle 310) of the blood collection pen 300 extends out of the first opening 220. In the accommodated state, the blood collection pen 300 may be substantially parallel to the first surface 230 of the body 200. In the operating state, the blood collection pen 300 may be substantially perpendicular to the first surface 230 of the body 200.

In some embodiments, as shown in FIG. 4, the blood collection pen 300 includes a front portion 330, a central portion 340 and a rear portion 350. In the accommodated state of the blood collection pen 300, the blood collection needle 310 is assembled on the rear portion 350 and a needle point of the blood collection needle 310 is accommodated into the front portion 330, so as to prevent the blood collection needle 310 from being polluted; the blood collection button 320 is disposed on the central portion 340; and the rear portion 350 is provided with a mechanical spring mechanism which is configured to eject the blood collection needle 310 under the actuation of the blood collection button 320. More specifically, one end of the mechanical spring mechanism is directly or indirectly connected with (for example, fixed on) the side of the blood collection needle 310 away from the needle point, and the other end of the mechanical spring mechanism abuts against the rear portion 350; the blood collection button 320 can be connected to (for example, fixed on) the mechanical spring mechanism through the central portion 340; and when the user performs blood sugar detection, the blood collection button 320 is operated to actuate the mechanical spring mechanism to eject the blood collection needle 310. It should be understood that the needle point of the blood collection needle 310 is an example of the end portion of the collecting part.

In some embodiments, the rear portion 350 adopts the design of recess so as to flexibly replace the blood collection needle 310.

Figure 5:
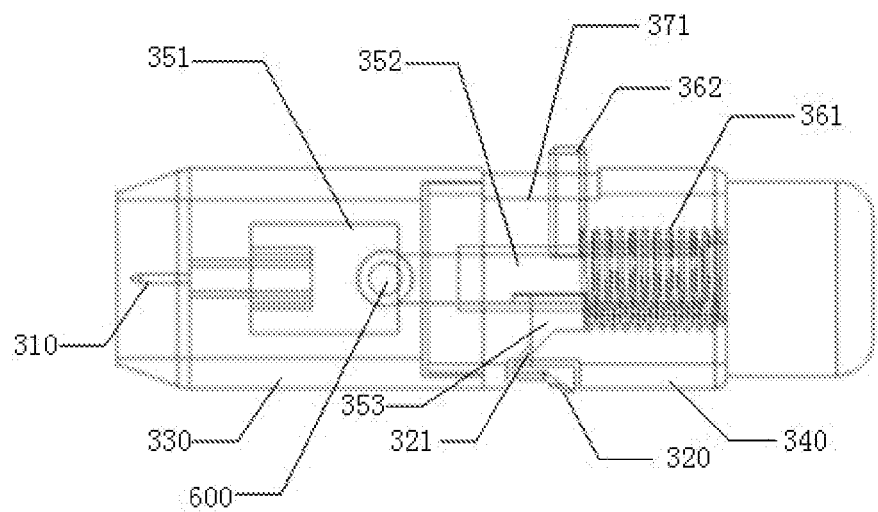
FIG. 5 is a schematic structural diagram of the blood collection pen of the blood sugar detection device provided by at least one embodiment of the present disclosure.
Figure 6:
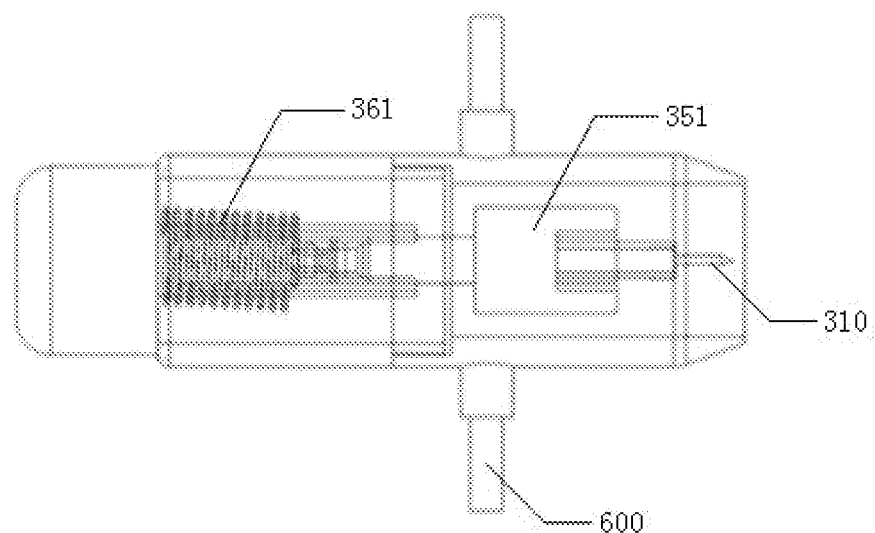
FIG. 6 is a schematic structural diagram of the blood collection pen of the blood sugar detection device provided by at least one embodiment of the present disclosure.

As shown in FIG. 5, in some embodiments, the mechanical spring mechanism includes a spring 361. The side of the spring 361 away from the blood collection needle 310 is connected to (for example, fixed on) the rear portion 350. The blood sugar detection device further comprises a base 352 which includes a mounting part 351. The blood collection needle 310 is assembled on the mounting part 351. The side of the spring 361 close to the blood collection needle 310 is connected to (for example, fixed on) the side of the base 352 away from the mounting part 351. More specifically, when the user assembles the blood collection needle 310 on the mounting part 351, the spring 361 is synchronously compressed. The blood collection button 320 may be connected to (for example, fixed on) the mechanical spring mechanism through the central portion 340; and the user operates the blood collection button 320 to actuate the spring 361 to eject the blood collection needle 310 to pierce the skin.

In some embodiments, as shown in FIG. 3, the test paper supplier 500 is configured to provide the test paper 520 at the position, corresponding to the blood collection needle 310 when the blood collection pen 300 is in the operating state, below the first opening 220 (namely the side of the first opening 220 away from the first groove 210) in the process of blood sugar detection, so as to timely collect blood when the blood collection needle 310 pierces the skin.

Figure 7:
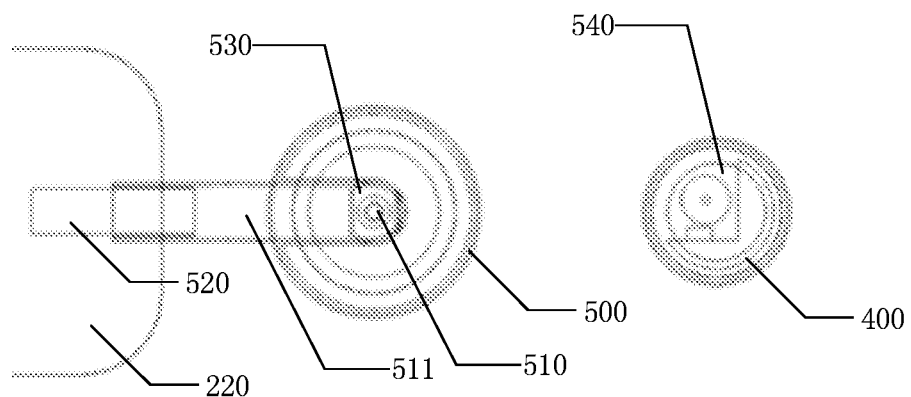
FIG. 7 is a schematic diagram illustrating the case where a test paper rotating shaft of the blood sugar detection device provided by at least one embodiment of the present disclosure is at the first position.
Figure 8:
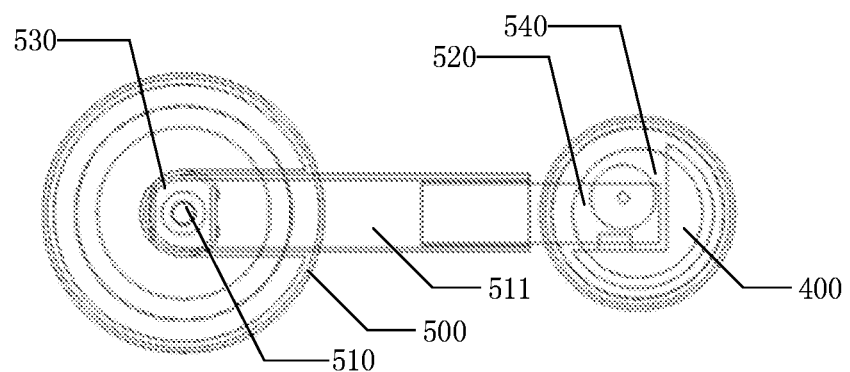
FIG. 8 is a schematic diagram illustrating the case where the test paper rotating shaft of the blood sugar detection device provided by at least one embodiment of the present disclosure is at the second position.

In some embodiments, the test paper supplier 500 includes a test paper rotating shaft 510. The test paper rotating shaft 510 is configured to accommodate the test paper 520 and allow the test paper 520 to extend out of a tail end of the test paper rotating shaft 510. The test paper rotating shaft 510 is rotatably mounted on the body 200, accommodates the test paper 520 into the blood sugar detector 400 when rotating to a first position (as shown in FIG. 7), and provides the test paper 520 at the position below the first opening 220 (namely the side of the first opening 220 away from the first groove 210) corresponding to the blood collection needle 310 of the blood collection pen 300 that is in the operating state when rotating to a second position (as shown in FIG. 8). As shown in FIGS. 2, 7 and 8, the test paper 520 is wound round the test paper rotating shaft 510; the test paper rotating shaft 510 includes an extension part 511; and the test paper 520 is capable of extending out of a tail end of the extension part 511 to collect blood. More specifically, when the user does not use the blood sugar detection device, the extension part 511 of the test paper rotating shaft 510 is rotated to the first position, and then the test paper 520 is accommodated into the blood sugar detector 400, so as to prevent the test paper 520 from being polluted. When the user uses the blood sugar detection device for blood sugar detection, the extension part 511 of the test paper rotating shaft 510 is rotated to the second position at first, and then the test paper 520 is rotated to the position below the first opening 220 (namely the side of the first opening 220 away from the first groove 210) corresponding to the blood collection needle 310 of the blood collection pen 300 that is in the operating state, to collect blood after the blood collection needle 310 pierces the skin; and subsequently, the extension part 511 of the test paper rotating shaft 510 is rotated to the first position, and the test paper 520 that has collected blood is accommodated into the blood sugar detector 400 for blood sugar detection.

As shown in FIGS. 7 and 8, in some embodiments, the test paper supplier 500 further includes a servo motor 530 which is disposed inside the body 200; and an output shaft of the servo motor 530 is connected with the test paper rotating shaft 510 to drive the test paper rotating shaft 510 to rotate the extension part 511 of the test paper rotating shaft 510 to the first position and the second position, and then the test paper 520 is rotated to the position below the first opening 220 (namely the side of the first opening 220 away from the first groove 210) or accommodated into the blood sugar detector 400. More specifically, the body 200 is also provided with a button (not shown) for controlling the operation of the servo motor 530. Thus, the operation of the blood sugar detection device is simpler, and the use experience of the user is improved. It should be understood that the servo motor 530 is an example of a driver for driving the test paper rotating shaft 510, and no limitation will be given here in the embodiments of the present disclosure.

In some embodiments, the blood sugar detector 400 is provided with a second opening 540 which is configured to allow the test paper 520 to extend into the blood sugar detector in the case where the extension part 540 of the test paper rotating shaft 510 is rotated to the first position. As shown in FIG. 2, the blood sugar detector 400 is a cylinder, and the second opening 540 is disposed on a side surface of the cylinder to form a curved opening, so that the test paper 520 may conveniently extend into the blood sugar detector 400 in the case where the extension part 540 of the test paper rotating shaft 510 is rotated to the first position, thereby preventing the test paper 520 from being damaged.

In some embodiments, as shown in FIG. 3, the body 200 further includes an accommodating part 700 which adopts the form of grids. More specifically, at least one partition, for instance, a plurality of partitions, may be disposed in the accommodating part 700, so as to conveniently accommodate components required for blood sugar detection, for instance, the blood collection needle 310 and alcohol cotton. The accommodating part 700 may be connected to (for example, fixed on) the body 200 through a locking device, so as to prevent the components in the accommodating part 700 from falling.

As shown in FIG. 5, in some embodiments, the rear portion 350 is provided with a partition plate 371 which is spaced from one end of the rear portion away from the blood collection needle 310. The mechanical spring mechanism further includes a pull rod 362. The pull rod 362 runs through the spring 361, is connected to (for example, fixed on) the base 352 on the side close to the blood collection needle 310, and movably runs through the partition plate. The spring 361 is confined between the partition plate and the base 352 by the partition plate. The pull rod 362 may stabilize the movement direction of the spring 361, so that the blood collection needle 310 may be stably ejected, and the service life of the blood collection pen 300 may be prolonged. More specifically, the spring 361 may include a first spring and a second spring; the rear portion 350 is provided with a first partition plate and a second partition plate; the first partition plate is configured to confine the first spring between the base 352 and the first partition plate; the second partition plate is configured to separate the second spring from the end of the rear portion 350 away from the blood collection needle 310; the radial length of the second spring is less than the radial length of a hole of the first partition plate, so that the second spring is capable of moving in the hole of the first partition plate. In the case where the user assembles the blood collection needle 310 on the rear portion 350, the first spring is synchronously compressed, and the blood collection button 320 is operated so that the first spring ejects the blood collection needle 310 to pierce the skin; the second spring is stretched by the first spring to generate a resilience force in the ejection process of the first spring, and the blood collection needle 310 is rapidly retracted; and then the automatic retraction of the blood collection needle 310 is realized.

In some embodiments, as shown in FIGS. 4 and 5, a clamping part or a clamp 353, configured to clamp a release end 321 of the blood collection button 320, is disposed on the base 352. More specifically, in the case where the user assembles the blood collection needle 310 on the mounting part 351, the spring 361 in the mechanical spring mechanism is synchronously compressed, and the clamping part 353 clamps the release end 321 of the blood collection button 320, so as to confine the blood collection needle 310 in the state to be ejected; and in the process of blood sugar detection, the user operates the blood collection button 320 to separate the clamping part 353 from the release end 321, and the spring 361 in the mechanical spring mechanism actuates the blood collection needle 310 to eject.

In some embodiments, a spring sheet (not shown in FIG. 4) is also disposed between the blood collection button 320 and the clamping part 353, and the release end 321 of the blood collection button 320 is capable of sliding on the spring sheet and is clamped by the clamping part 353 when sliding to a first positioning point. More specifically, in the case where the user synchronously compresses the spring 361 in the mechanical spring mechanism while assembling the blood collection needle 310 on the mounting part 351, the release end 321 of the blood collection button 320 is clamped by the clamping part 353 when sliding on the spring sheet from a second positioning point to the first positioning point, and the blood collection needle 310 is confined in the to-be-ejected state. In the process of blood sugar detection, the user presses the blood collection button 320, and the release end 321 is separated from the clamping part 353 under the action of the spring sheet, and then the spring 361 in the mechanical spring mechanism actuates the blood collection needle 310 to eject.

In some embodiments, the carrier 100 includes a wristlet. By adoption of the wristlet as the carrier 100, the user may wear the blood sugar detection device on the wrist, so the blood sugar detection device is convenient to carry. Moreover, when the blood sugar detection device is worn on the wrist, blood may be collected by rotating the blood collection pen 300, and the blood sugar may be detected through the blood sugar detector 400, without taking off the blood sugar detection device, so the operation is simple and the use experience of the user is improved.

In some embodiments, as shown in FIG. 1, the body 200 further includes a display 800 which is on the side of the body 200 away from the body of the user and configured to display a blood sugar detection result, so as to facilitate the viewing of the user. More specifically, the display 800 may be an organic light-emitting diode (OLED) display, a liquid crystal display (LCD) or the like, and the display content may be the glycemic index, the current time, etc. No specific limitation will be given here.

The following should be noted:

(1) The accompanying drawings involve only the structure(s) in connection with the embodiment(s) of the present disclosure, and other structure(s) can be referred to common design(s).

(2) For the purpose of clarity only, in accompanying drawings for illustrating the embodiment(s) of the present disclosure, the thickness and size of a layer or a structure may be enlarged. However, it should understood that, in the case in which a component or element such as a layer, film, area, substrate or the like is referred to be "on" or "under" another component or element, it may be directly on or under the another component or element or a component or element is interposed therebetween.

(3) In case of no conflict, features in one embodiment or in different embodiments can be combined.

The foregoing are merely exemplary embodiments of the disclosure, and not intended to define the scope of the disclosure, and the scope of the disclosure is determined by the appended claims.

What is claimed is:

1. A detection device, comprising:
   a body, comprising a first groove and a first opening, wherein the first opening is on a first surface of the body and in communication with the first groove;
   a collector, configured to be at least partially accommodated in the first groove in a rotatable manner and being capable of rotating to allow at least part of the collector to extend out of the first opening in a process of detection;
   a test paper supplier, disposed on the first surface and configured to provide a test paper on a side of the first opening away from the first groove in the process of detection so as to collect a detection sample; and
   a detector, disposed on the first surface and configured to detect a property of the detection sample collected on the test paper;
   the collector further comprises a first rotating shaft, and the collector is pivotably connected with the body through the first rotating shaft;
   the collector further comprises a collecting part and a button operably connected to the collecting part, the button is disposed on a side of the collector facing the first surface in a case where the collector is in an accommodated state, wherein in the accommodated state, the collector is accommodated into the first groove, and the button is exposed in a case where the collector rotates to be in an operating state.

2. The detection device according to claim 1, wherein the collector further comprises a front portion, a central portion and a rear portion,
   in a case where the collector is in the accommodated state, the collecting part is assembled on the rear portion, and an end portion of the collecting part is accommodated in the front portion;
   the rear portion comprises a mechanical spring mechanism which is configured to eject the collecting part towards the front portion under an actuation of the button; and
   the button is disposed on the central portion and operably connected with the mechanical spring mechanism.

3. The detection device according to claim 2, wherein the rear portion comprises a recess structure.

4. The detection device according to claim 2, wherein the mechanical spring mechanism comprises a spring, and a side of the spring away from the collecting part is connected to the rear portion; and
   the detection device further comprises a base, wherein the base comprises a mounting part configured to assemble the collecting part, and
   a side of the spring close to the collecting part is connected to a side of the base away from the mounting part.

5. The detection device according to claim 4, wherein the rear portion comprises a partition plate which is spaced from an end of the rear portion away from the collecting part, so as to confine the spring between the partition plate and the base;

the mechanical spring mechanism further comprises a pull rod, wherein the pull rod extends through the spring and is connected to the base on a side close to the collecting part, and the pull rod movably extends through the partition plate.

6. The detection device according to claim 5, wherein the test paper supplier further comprises a driver which is configured to be connected with a test paper rotating shaft to drive the test paper rotating shaft to rotate.

7. The detection device according to claim 6, wherein the driver comprises a servo motor, wherein the servo motor comprises an output shaft which is connected with the test paper rotating shaft.

8. The detection device according to claim 6, wherein the detector comprises a second opening which is configured to allow the test paper to extend into the detector in a case where the test paper rotating shaft rotates to a first position.

9. The detection device according to claim 5, wherein
the button comprises a release end; and
the base comprises a clamping part, wherein the clamping part is configured to clamp the release end of the button.

10. The detection device according to claim 1, wherein the test paper supplier is configured to provide, in the process of detection, the test paper on the side of the first opening away from the first groove and at a position corresponding to the collecting part of the collector that is in the operating state.

11. The detection device according to claim 1, wherein the test paper supplier comprises a test paper rotating shaft; and the test paper rotating shaft is configured to accommodate the test paper and allow the test paper to extend out of a tail end of the test paper rotating shaft, and the test paper rotating shaft is also configured to be rotatably connected to the body.

12. The detection device according to claim 11, wherein the test paper rotating shaft is configured to:
accommodate the test paper into the detector in a case where the test paper rotating shaft rotates to a first position, and
provide the test paper on the side of the first opening away from the first groove and at the position corresponding to the collecting part of the collector that is in the operating state in a case where the test paper rotating shaft rotates to a second position.

13. The detection device according to claim 1, wherein the body further comprises an accommodating part which comprises at least one partition.

14. The detection device according to claim 1, further comprising a carrier, wherein the carrier is configured to carry the body.

15. The detection device according to claim 14, wherein the carrier comprises a wristlet.

16. The detection device according to claim 1, wherein the body further comprises a display which is on a side of the body away from the first surface and configured to display a detection result.

* * * * *